United States Patent [19]

Bao et al.

[11] Patent Number: 5,534,028
[45] Date of Patent: Jul. 9, 1996

[54] HYDROGEL INTERVERTEBRAL DISC NUCLEUS WITH DIMINISHED LATERAL BULGING

[75] Inventors: Qi-Bin Bao; Paul A. Higham, both of New York, N.Y.

[73] Assignee: Howmedica, Inc., New York, N.Y.

[21] Appl. No.: 49,820

[22] Filed: Apr. 20, 1993

[51] Int. Cl.⁶ ............................................. A61F 2/44
[52] U.S. Cl. ............................................. 623/17; 606/61
[58] Field of Search ..................... 623/8, 7, 17, 16, 623/18, 11; 606/61–64

[56] References Cited

U.S. PATENT DOCUMENTS

| | | |
|---|---|---|
| 3,867,728 | 2/1975 | Stubstad et al. . |
| 3,875,595 | 4/1975 | Froning et al. . |
| 4,180,308 | 12/1979 | Mancini et al. . |
| 4,309,777 | 1/1982 | Patil . |
| 4,349,921 | 9/1982 | Kuntz . |
| 4,714,469 | 12/1987 | Kenna . |
| 4,772,287 | 9/1988 | Ray et al. . |
| 4,863,477 | 9/1989 | Monson ........................... 623/17 |
| 4,904,260 | 2/1990 | Ray et al. . |
| 4,911,718 | 3/1990 | Lee et al. . |
| 4,932,969 | 6/1990 | Frey et al. . |
| 5,047,055 | 9/1991 | Bao et al. ........................ 623/17 |

FOREIGN PATENT DOCUMENTS

| | | |
|---|---|---|
| 0356112 | 2/1990 | European Pat. Off. . |
| 0505634 | 9/1992 | European Pat. Off. . |
| WO-9316664 | 9/1993 | WIPO . |

OTHER PUBLICATIONS

Lee, C. K. et al., "Fiber–Reinforced Functional Disc Prosthesis," 35th Annual Meeting, Orthopaedic Research Society, Feb. 6–9, 1989, Las Vegas, Nevada.

McNally, D. S. et al., "Internal Intervertebral Disc Mechanics as Revealed by Stress Profilometry," *Spine*, 17, No. 1, pp. 66–73 (1992).

Zimmerman, M. C. et al., "The Mechanical Properties of the Canine Lumbar Disc and Motion Segment," *Spine*, 17, No. 2, pp. 213–220 (1992).

International Search Report mailed May 16, 1994.

*Primary Examiner*—Debra S. Brittingham
*Attorney, Agent, or Firm*—Peter C. Richardson; Lawrence C. Akers; Elizabeth O. Slade

[57] ABSTRACT

A prosthetic nucleus for a vertebral disc is made of a hydrogel material. The hydrogel prosthetic nucleus has a shape generally conforming to the natural nucleus pulposus, and it exhibits diminished lateral bulging under high compressive loads. The hydrogel has a water content of from 30% to 90% and has a compressive strength of 4 MNm$^{-2}$ or greater. When the hydrogel material is dehydrated, it has a dimension of less than half of that of the hydrated hydrogel nucleus. The prosthetic nucleus may be formed of two or more pieces of hydrogel material which pieces, when combined, have a shape generally conforming to the natural nucleus. The prosthetic nucleus may have a stiff posterior periphery and/or a thickened anterior wall.

4 Claims, 8 Drawing Sheets

HYDROGEL INTERVERTEBRAL DISC NUCLEUS WITH DIMINISHED LATERAL BULGING

BACKGROUND OF THE INVENTION

1. Field of the Invention

This invention relates to a prosthetic intervertebral disc nucleus. More particularly it relates to an artificial disc nucleus made of a hydrogel material that exhibits diminished lateral bulging at certain sections of the nucleus and/or diminished narrowing under high compressive load.

2. Description of the Prior Art

The intervertebral disc is a complex joint anatomically and functionally. It is composed of three structures: the nucleus pulposus (hereinafter referred to as the "natural nucleus"), the annulus fibrosus and the vertebral end-plates.

Degeneration of an intervertebral disc, often due to aging, is believed to be a common cause of back pain. An additional cause of back pain is displacement of an intervertebral disc. In either of these cases, the nucleus pulposus may herniate and/or protrude into the vertebral canal or intervertebral foramen. Most herniations and protrusions occur on the posterior or posterior/lateral side of the disc where the disc annulus is generally thinner and weaker than on the anterior side. The disc may in turn press upon the spinal nerve that exits the vertebral canal through the partially obstructed foramen, causing pain or paralysis in the area of its distribution.

Degenerated or displaced discs may be treated by replacing the entire natural disc with an artificial disc. Various artificial discs are disclosed in the following U.S. Pat. Nos.: 3,867,728 to Stubstad et al.; 3,875,595 to Froning; 4,309,777 to Patil; 4,714,469 to Kenna; 4,349,921 to Kuntz; 4,772,287 to Ray et al.; 4,904,260 to Kuntz; 4,911,718 to Lee et al; and 4,932,969 to Frey et al. (All of the documents cited herein, including the foregoing, are hereby incorporated in this application in their entireties.)

Alternatively, degenerated or displaced discs may be treated by replacing only the natural nucleus rather than the entire disc. U.S. Pat. No. 5,047,055 to Bao et al. relates to a prosthetic nucleus for a vertebral disc. The prosthetic nucleus is made of a hydrogel material which, when dehydrated, has a dimension of less than half of that of the hydrated hydrogel nucleus. It may be implanted in the dehydrated state, and when fully hydrated it has a size and shape generally conforming to a natural nucleus. The shaped hydrogel has a much higher structural integrity than the natural nucleus because it has shape memory due to cross-linking or strong hydrogen bonding in the polymer matrix. However, it still exhibits extensive lateral bulging under high compressive load if there is no boundary to constrain the deformation. As used in this application, lateral bulging means bulging that occurs along the side perimeter of the nucleus.

Normally, insertion of a shaped hydrogel prosthetic nucleus does not require removal of the disc annulus or end-plates so lateral bulging of the hydrogel nucleus is restricted by the restoring force of the stretched annulus fibers and the external force of the end plates. Also, due to its structural integrity, the hydrogel nucleus will generally not herniate or bulge through previously herniated areas or through incisions which were made to remove the degenerated nucleus. However, in some cases incisions or previously herniated areas will be particularly large, or the restoring force of annulus fibers will be diminished due to fiber damage. In such cases it is important that lateral bulging of a shaped hydrogel be diminished in order to prevent further herniation or fiber damage.

SUMMARY OF THE INVENTION

It is an object of this invention to provide a prosthetic nucleus for a disc which is composed of a hydrogel material capable of balancing its hydrostatic pressure with external loads thereon and which does not have extensive lateral bulging under high compressive load. It is another object of this invention to diminish bulging along specific sections of the nucleus such as at the posterior side of the nucleus and/or at the side of the nucleus corresponding to the location of damaged annulus fibers. It is another object of this invention to provide a process for making a prosthetic nucleus which does not have extensive lateral bulging under high compressive load, or which has diminished bulging along specific sections of the nucleus.

Broadly, the present invention relates to a prosthetic nucleus for implanting into a disc space after removal of a degenerated or damaged nucleus of an intervertebral disc. The prosthetic nucleus may comprise a biologically compatible hydrogel material having, when fully hydrated, a size and shape generally conforming to a natural nucleus or to the shape of a cavity created after removal of the degenerated or damaged nucleus; a water content of from about 30% to about 90%; and a compressive strength of about 4 $MNm^{-2}$ or greater. At least part of the nucleus periphery exhibits diminished lateral bulging in comparison to other parts of the nucleus periphery. Preferably, the unrestrained lateral bulging along at least part of the nucleus periphery is less than about 4.00 mm when under a compressive load of 10 N. In a preferred embodiment, the nucleus comprises a biologically compatible hydrogel material having when fully hydrated a size and shape generally conforming to a natural nucleus; a water content of from 30% to 90%; and a compressive strength of 4 $MNm^{-2}$ or greater; wherein the modules of the nucleus is from 0.1 to 1.5 MPa and the modulus of the nucleus varies such that at least part of the nucleus periphery has a modulus of at least 10% more than the softest part of the nucleus; and wherein the nucleus periphery wall varies in height by at least 1 mm. In another preferred embodiment, the unrestricted lateral bulging along the entire nucleus periphery is less than about 4 mm when under a compressive load of 10 N.

The present invention also relates to methods for forming a prosthetic nucleus. One method comprises the steps of: (a) forming a mass of bonded biocompatible hydrogel material having a water content when fully hydrated of from about 30% to about 90% and a compressive strength of about 4 $MNm^{-2}$ or greater; (b) shaping the mass of hydrogel to a shape generally conforming to a natural human disc nucleus; and (c) stiffening at least part of the periphery of the nucleus. A second method comprises forming a mass of bonded biocompatible hydrogel material by separating central and periphery areas of the nucleus with a diaphragm and injecting a first liquid monomer into the central area and a second liquid monomer into the periphery area, wherein the liquid monomers harden into gels such that the first monomer yields a softer gel than the second monomer. A third method comprises the steps of: (a) forming a mass of bonded biocompatible hydrogel material having a water content when fully hydrated of from about 30% to about 90% and a compressive strength of about 4 $MNm^{-2}$ or greater; and (b) shaping the wall of hydrogel to a shape generally conforming to a natural human disc nucleus wherein the anterior wall is at least about 1 mm thicker than the posterior wall. A fourth method is a method for forming a prosthetic nucleus having a periphery and a center, the periphery comprising a first part and a second part wherein the first part has less unrestricted lateral bulging than the second part, said method comprising: (a) orienting a nucleus mold such that the first part of the periphery is below the second part of the periphery; (b) pouring more than one PVA solution into the mold, wherein at least two PVA solutions have different densities; (c) allowing the PVA solutions to harden to form a prosthetic nucleus; and (d) removing the hardened prosthetic nucleus from the mold.

The hydrogel prosthetic nucleus will generally have a shape and size conforming to the natural nucleus which has been removed in a regular discectomy procedure and has a water content of at least about 30%, preferably about 70 to about 85%, and optionally up to about 90%, with a compressive strength of at least about 4 Meganewton per square meter ($MNm^{-2}$) or greater when hydrated to its equilibrium water content. Preferably, at least part of the nucleus external surface is stiffer than other external sections. It is especially preferred to have a stiff posterior periphery or a stiff section near the area where an annulus has shown some weakening either due to damage or due to surgical incision.

In another preferred embodiment, one wall section of the nucleus is thicker than another wall section in order to diminish lateral bulging of the thinner wall section. In more preferred embodiments, the anterior wall section of the nucleus is thicker than the posterior wall section in order to diminish lateral bulging of the posterior periphery.

In another preferred embodiment, one wall section of the nucleus is both thicker and less stiff than another wall section in order to diminish lateral bulging of the thinner/stiffer wall section. In more preferred embodiments, the anterior wall section of the nucleus is both thicker and less stiff than the posterior wall section in order to diminish lateral bulging of the posterior periphery.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings similar reference characters denote similar elements throughout the several views, in which.

FIG's 11 (a) and (b) are isometric and schematic views, respectively, of a prosthetic nucleus of the present invention showing the dimensions of the nucleus before and after loading.

FIG's 12 (a) and (b) are isometric and schematic views, respectively, of a prosthetic nucleus of the present invention showing the stiffness of the present invention and the dimensions of the nucleus after loading.

FIG's 13 (a) and (b) are isometric and schematic views, respectively, of a prosthetic nucleus of the present invention showing the dimensions and stiffness of the nucleus before and after loading.

DESCRIPTION OF THE PREFERRED EMBODIMENT

Referring to FIGS. 1 through 14, in the preferred embodiment the prosthetic nucleus of the present invention generally denoted as 10 is shaped to conform, when hydrated, to the general shape of the natural nucleus. The nucleus is implanted in disc 12 of vertebrae 14 and is surrounded by the natural annulus fibrosus 16. Vertebral end plates 20 and 22 cover the superior 34 and inferior 36 faces of nucleus 10 respectively. The posterior periphery 24 is preferably stiffer than the anterior periphery 26. The preferred material of nucleus 10 is a hydrogel material, preferably highly hydrolysed polyvinyl alcohol (PVA).

It has been reported in the literature (Lee et al., *Fiber-Reinforced Functional Disc Prosthesis.*, 35th Annual Meeting, Orthop. Res. Soc., 1989; and Zimmerman et al., *The Mechanical Properties of the Canine Lumbar Disc and Motion Segment,* Spine, 17, No. 2, p. 213, 1992) that the modulus of the natural human lumbar spine is in the range of from 7.42 to about 15 MPa. In order to avoid excessive compressive stress on the central area of the vertebral body made of cancellous tissue, it is desirable to have the modulus of the hydrogel nucleus less than that of the disc, although the modulus of the hydrogel nucleus may be slightly higher than that of the human lumbar disc because the average stress on the nucleus of a healthy disc is higher than that on the annulus. (McNally and Adams, *Internal Intervertebral Disc Mechanics as Reviewed by Stress and Profilometry,* Spine, 17, p. 66, 1992.) Excessive stress on the nucleus implant could cause damage on the endplate and result in the development of Schmorl's nodes. Accordingly, the anterior periphery 26 will preferably have a stiffness of from about 0.1 to about 1.5 MegaPasquals (MPa), and the posterior periphery 24 will preferably have a stiffness at least about 10% less than that of the anterior periphery 26, more preferably more than about 30% less than that of the anterior periphery 26. The increase in stiffness from the anterior to posterior sides of the hydrogel implant can be either gradual or sudden. (As used herein, stiffness and softness are expressed as a modulus in units of MegaPasquals (MPa).)

The nucleus of the present invention may have diminished lateral bulging such that the unrestrained lateral bulging along at least part of the nucleus periphery under a compressive load of 10 N is less than about 4.00 mm, preferably about 0.50–3.00 mm, and especially preferably about 0.70–1.50 min.

The disc height under normal compression loads at different positions of the disc will generally vary. At upper lumbar levels, for instance, the two adjacent vertebral bodies are quite parallel, while at lower lumbar levels, especially at L5-S1 disc, the disc exhibit a wedge shape with anterior height larger than posterior height. This geometry should be taken into consideration in determining the dimensions of the prosthetic nucleus. It is preferred that the anterior wall 28 will be at least 1 mm thicker than the posterior wall 30, more preferably 2–3 mm thicker.

The expansion factor of a dehydrated hydrogel will be dependent upon equilibrium water content (EWC) of that hydrogel. It may vary from 1.19 for a hydrogel of 38% EWC to 1.73 for a hydrogel of 80% EWC. For an 80% EWC hydrogel, the volume of the dehydrated prosthetic nucleus is only about 20% of the hydrated one.

After hydration in the disc, the hydrogel nucleus will generally be constrained tightly in the cavity from which the nucleus has been excised. The constraining forces are the restoring force of the stretched annulus fibers and the external force through the end-plates. The constraint from the annulus and the end-plates will generally restrict the movement of the hydrogel nucleus and prevent it from bulging and herniating from the cavity. However, in cases where previously herniated areas or incisions are particularly large, or where the restoring force of the stretched fibers is diminished due to fiber damage, bulging and herniation are diminished or prevented by the diminished lateral bulging of the present invention.

The prosthetic nucleus may be formed from two or more pieces of hydrogel material, each shaped so that when combined they have a shape generally conforming to the natural nucleus. Utilizing a two-piece prosthetic nucleus facilitates implantation, which is done with the hydrogel material in a dehydrated or unhydrated state. In preferred embodiments one piece will be softer (less stiff) than the other, and the stiffer piece can be implanted in the posterior position.

The general technique of preparing PVA hydrogel from the commercially available PVA powder has been disclosed in the U.S. Pat. No. 4,663,358. Typically, 10–25% PVA powder is mixed with a solvent, such as water, dimethyl sulfoxide, ethylene glycol or a mixture thereof. The slurry is then heated and shaken until a uniform gel is formed. The gel is then poured or injected into either a metal, plastic or rubber mold which will give the shape and the size of the prosthetic nucleus. After cooling the gel below $-10°$ C. for crystallization for several hours, the shaped PVA gel will be soaked and rinsed with water until all the organic solvent has been exchanged with water. The hydrated PVA gel can then be dehydrated for implantation. The PVA hydrogels thus prepared will have a water content between 60–90% and modulus from 0.07–1.33 MPa as shown in Table 1.

While PVA is used in the preferred prosthetic disc, other hydrogels such as lightly cross-linked polymers of 2-hydroxyethyl methacrylate, or copolymers and terpolymers made from the combination of the monomers of an N-vinyl monomer, (for example, N-vinyl-2-pyrrolidone (N-VP)), a hydroxy alkyl methacrylate ester, (for example, 2-hydroxylethyl methacrylate (HEMA)), an alkyl methacrylate (for example, methyl methacrylate (MMA)), an ethylenically unsaturated acid (for example, methacrylic acid (MA)) and an ethylenically unsaturated base (for example, N,N-diethylamino ethyl methacrylate (DEAEMA)) may be used.

HYPAN™ (hydrogel polyacrylonitrile) is another type of hydrogel which can be used as a hydrogel nucleus. This hydrogel, unlike the cross-linked hydrogel, has a multiblock copolymer (MBC) structure with hard crystalline nitrile blocks which gives the hydrogel good mechanical properties and soft amorphous hydrophilic blocks which gives the hydrogel good water binding capability. The methods of preparing the HYPAN™ hydrogels of different water contents and different mechanical properties have been disclosed in the U.S. Pat. Nos. 4,337,327, 4,370,451, 4,331,783, 4,369,294, 4,420,589, 4,379,874 and 4,631,188. The device of this material can be either melt compressed as thermoplasts or injection molded.

In general, any hydrogel that can be used for soft contact lenses can be used as long as the hydrogel exhibits a compressive strength of at least 4 $MNm^{-2}$. Most of these materials have been FDA approved for use as contact lenses. Of course, many other hydrogel compositions may be used since, unlike contact lenses, opaque materials are acceptable. The art of preparing these polymers and copolymers has been disclosed in numerous U.S. patents. The water content of these hydrogels can vary from 38% for polymacon (poly HEMA) to 79% for lidofilcon B (copolymer of N-VP and MMA).

A prosthetic nucleus made from these hydrogels can be prepared, for instance, by cast molding or machine cutting. In cast molding, the liquid monomer mixture with initiator or polymer solution is poured into a mold of the predetermined shape and size. It is then cured in the mold. In the case of machine cutting, the polymer can be prepared in a similar manner in the form of a block or rod which is larger than the prosthetic nucleus. The polymer then will be cut to the shape and size of the nucleus. In both cases, the hydrogel expansion/shrinkage factor due to polymer swelling upon hydration has to be taken into account in determining the dimensions of the mold or of the cut prosthetic nucleus.

The present invention contemplates a nucleus wherein all or only part of the nucleus periphery exhibits diminished lateral bulging under high compressive load. In some cases a patient will have extensive damage to the annulus fibrosus and vertebral end-plates so it will be beneficial to insert a prosthetic nucleus with diminished bulging along the entire periphery. This can be achieved by making the entire nucleus periphery stiffer than the nucleus center. More typically, however, diminished lateral bulging will only be required along the part of the nucleus periphery corresponding to a particular weakness in the annulus fibrosus or vertebral end-plates, or to compensate for a particularly large incision or herniated area. Most typically, diminished lateral bulging will be required only on the posterior side because that is where most herniations occur. Lateral bulging can be reduced on the posterior side, for instance, by making the posterior periphery stiffer than the anterior periphery and/or by making the anterior wall thicker than the posterior wall. When the anterior wall is thicker than the posterior wall, the anterior wall will tend to absorb more compression load so that bulging will tend to occur on the anterior side rather than the posterior side.

Figure 4:
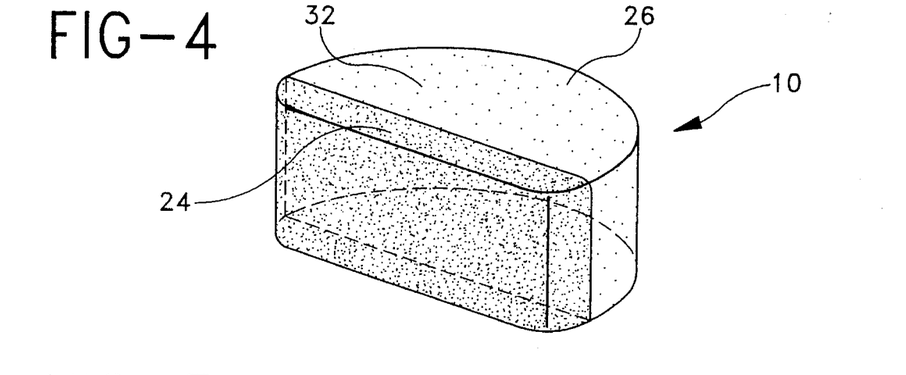
FIG. 4 is an isometric view of a prosthetic nucleus of the present invention showing a stiff periphery on the posterior side.
Figure 14:
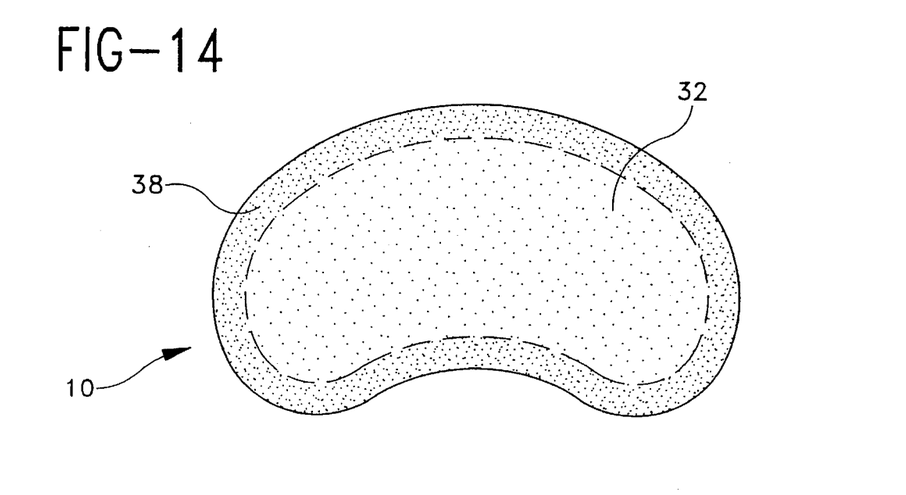
FIG. 14 is a top view of a prosthetic nucleus of the present invention.

With reference to FIG's 4 and 14, a nucleus 10 with a stiff periphery can be made by a cast molding process by separating the central area 32 and periphery area 24, 38 with a diaphragm. The diaphragm may be made of any suitable material such as metal or plastic, and the diaphragm will preferably be thin. Two different liquid monomer mixtures are then injected into these two areas such that the monomer mixture providing a stiffer gel is injected in the peripheral area 24, 38 and the monomer mixture providing a softer gel is injected in central area 32. Preferably, the shrink coefficients of these two gels will be close to avoid significant internal stress in the implant during equilibration in the saline. The diaphragm can then be removed while the solutions are close to gel point. Generally, there will not be extensive diffusion between the gels after removal of the diaphragm because of the gels' high viscosity. Local penetration of the gels is preferable to make a strong adhesion between the two sections.

An alternative way to prepare a stiff posterior nucleus is to mold two PVA hydrogels of different stiffness together. The density of PVA solutions that yield gels with higher stiffness is normally higher than PVA solutions that yield gels with lower stiffness. Also, the PVA solutions at concentrations of from 10–25% at 60°–100° C. are very viscous. Thus, when two different PVA solutions are poured into a mold, the denser solution (which will yield a stiffer gel) will generally sink to the bottom. If the mold is oriented such that the posterior side is at the bottom, then the implant will have a stiffer posterior wall. The adhesion between two sections of different density PVA will normally be very good.

A nucleus 10 with a stiff periphery can also be made by annealing techniques. For instance, a nucleus having a stiff posterior periphery can be prepared by first cast molding or lathe cutting a nucleus, and then heating the posterior periphery by dipping the posterior wall into an oil bath having a temperature of from about 80° to about 150° C. for several minutes or longer depending on the temperature. Typically, it is sufficient to dip the posterior wall into a 120° C. oil bath for from about 1 to about 10 or more minutes. It is believed that such heating causes the heated PVA to become more crystallized and therefore stiffer than the unheated portion.

A nucleus having different wall thicknesses can be made by either cast molding or cutting methods. In cast molding, the mold will generally be made with anterior wall thickness of about 1 mm or more than the posterior wall thickness for the disc as measured by either computer tomography (CT) or magnetic resonance imaging (MRI) scans. In the cutting method, the extra thickness of the anterior wall can be less than about 1 mm because after swelling the difference in thickness on the implant will increase proportionally.

Figures 1, 2:
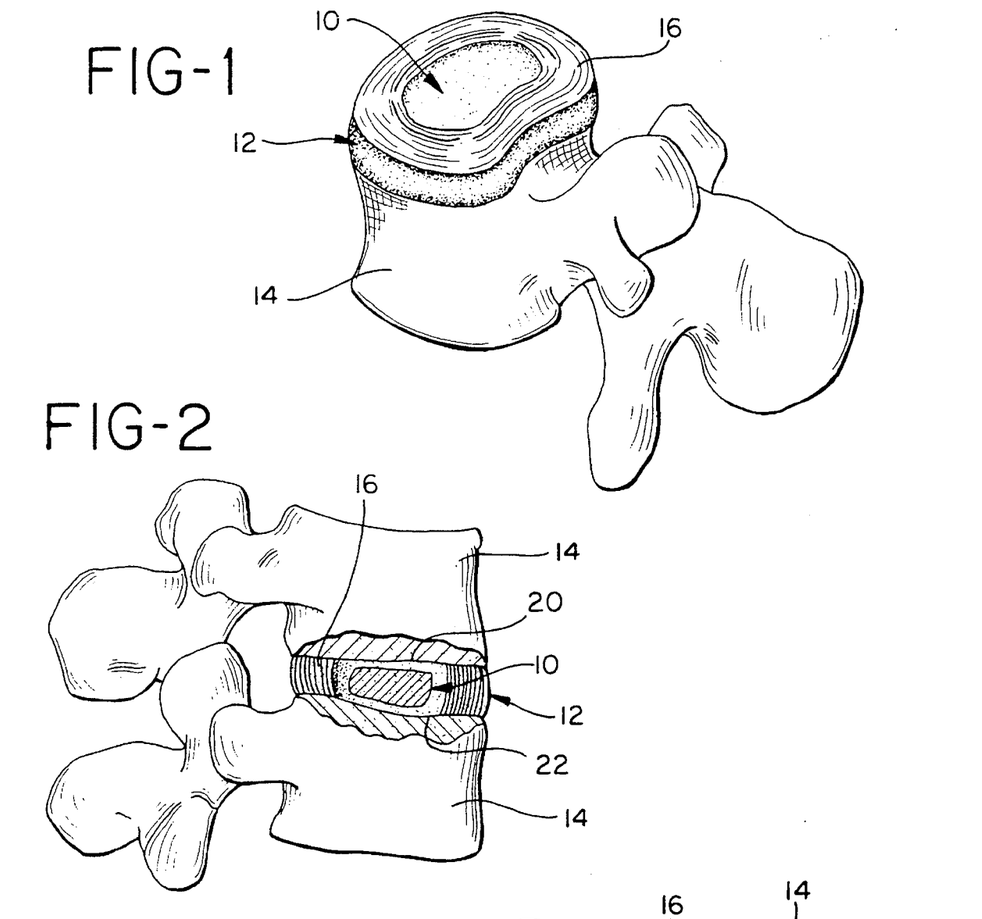
FIG. 1 is an isometric view of a single vertebral disc with the nucleus exposed.
FIG. 2 is an elevation view, partially in cross-section, of a disc with the prosthetic nucleus of the present invention shown in the dehydrated state.
Figure 3:
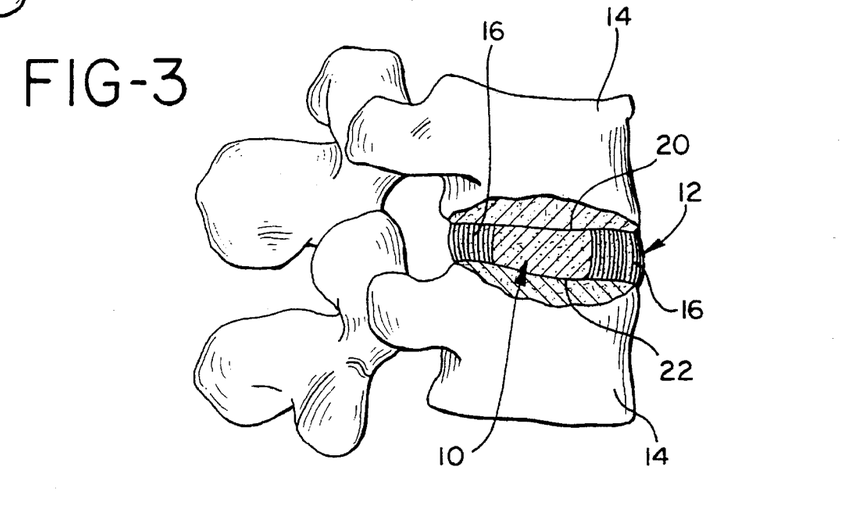
FIG. 3 is the disc of FIG. 2 showing the prosthetic nucleus of the present invention in the hydrated state.

Prosthetic nuclei 10 of various shapes can be designed as required to restore the function of the degenerated disc. In the preferred embodiment, the prosthetic nucleus approximates the shape and size of the natural nucleus, resembling an eclipse as shown in FIG. 1. The exact size and shape of the hydrated prosthetic nucleus can vary for different individuals and according to the disc level on which the implant will be inserted. A typical adult nucleus will be about 17 mm in semi-minor axis and about 30 mm in semi-major axis and about 11 mm in thickness.

Figure 5:
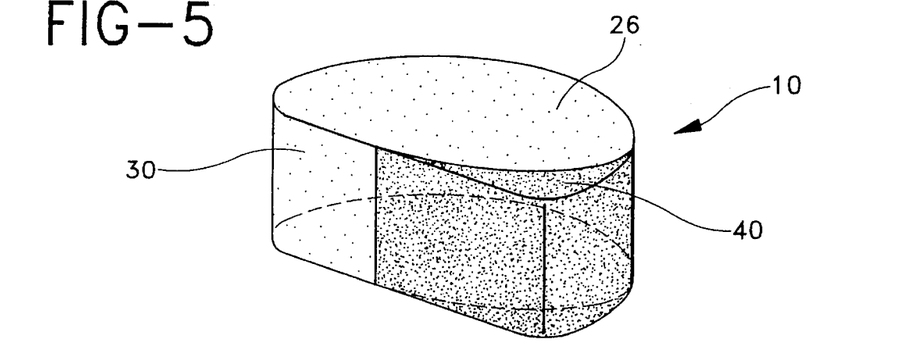
FIG. 5 is an isometric view of a prosthetic nucleus of the present invention showing a stiff section posterior-lateral side to protect a weakened annulus.

FIG. 4 shows a nucleus 10 with a stiff posterior periphery 24. The stiff hydrogel material is represented by the dense dot matrix. Posterior periphery 24 will generally be at least 10% stiffer than the other parts of the nucleus 10 such as the central area 32 or the anterior periphery 26. FIG. 5 shows a nucleus 10 with a stiff posterior-lateral 40 side. Such a nucleus 10 could protect a weakened annulus. Again, the stiff hydrogel material is represented by the dense dot matrix.

Figure 6:
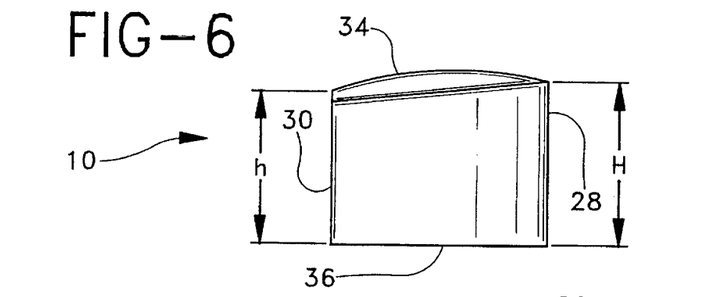
FIG. 6 is a side view of a prosthetic nucleus of the present invention showing a thick anterior wall.
Figure 7:
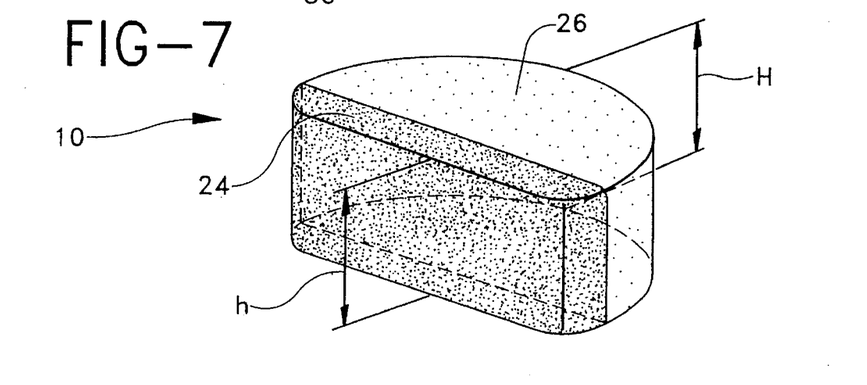
FIG. 7 is an isometric view of a prosthetic nucleus of the present invention showing a stiff periphery on the posterior side and a thick anterior wall.

FIG. 6 is a side view of a prosthetic nucleus with a thick anterior wall 28. The anterior wall height H will be greater than the posterior wall height h, preferably more than 1 mm greater and especially preferably from 2–3 mm greater. The superior 34 and inferior 36 sides of the nucleus are shown. In embodiments where one wall is thicker than the others, the anterior wall will generally be thicker than the posterior wall to diminish bulging on the posterior side. However, in some cases other walls (such as the posterior) will be made thicker to meet the specific needs of the patient. FIG. 7 shows a preferred embodiment for diminishing bulging on the posterior periphery. The posterior periphery 24 is made of a stiffened hydrogel material as indicated by the dense dot matrix, and the posterior wall 30 height (h) is less than the anterior wall 28 height (H).

Figures 8, 9:
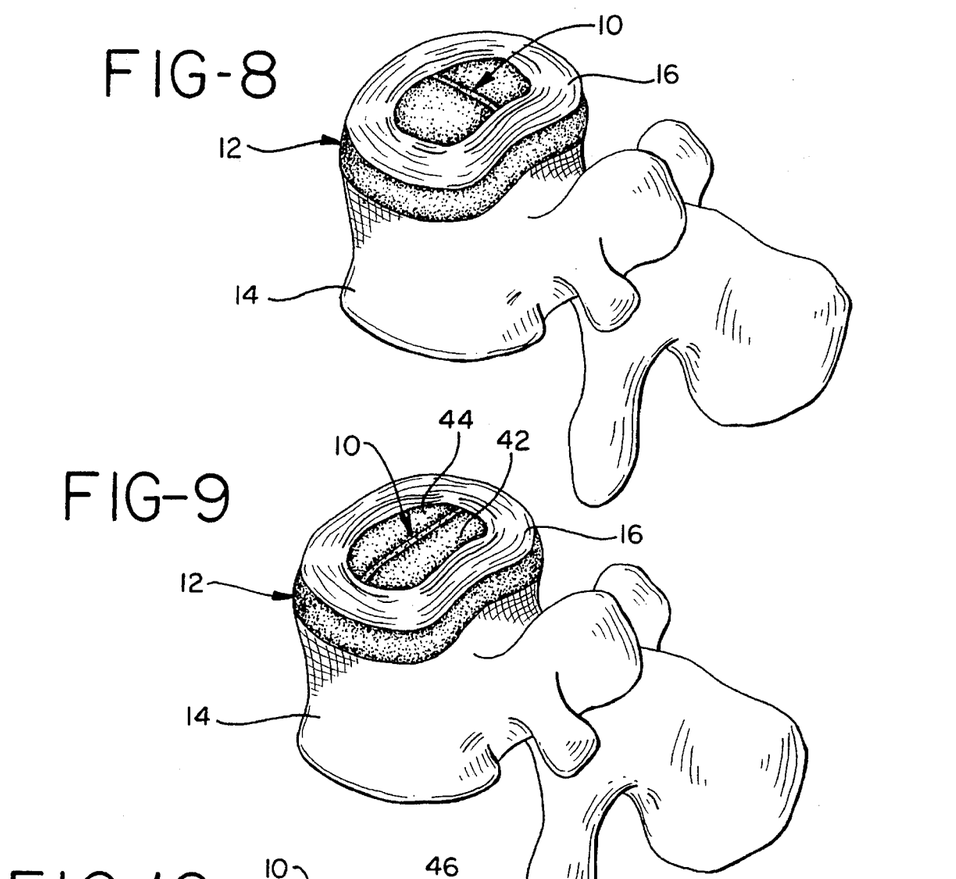
FIGS. 8 through 10 show three embodiments of a two-part prosthetic nucleus of the present invention in the hydrated state implanted within a vertebrae.
Figure 10:
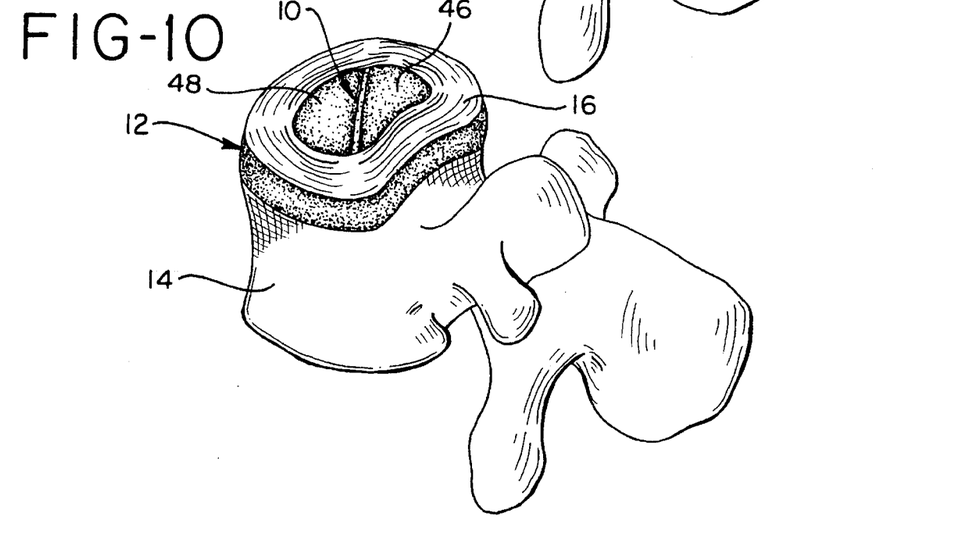

In an alternate embodiment shown in FIGS. 8–10, the prosthetic nucleus has two halves having the combined shape of a natural nucleus. Several designs of the two-part implants can be used. The first one of these is made by dividing the nucleus longitudinally (FIG. 8). The other is made by dividing the nucleus transversely (FIG. 9). Another design is to divide two halves laterally (FIG. 10). The major advantage of the two-part design is that the incision area can be further reduced and it is easier to manipulate the implants during surgery. In preferred embodiments, the posterior half 42 will be made of a stiffer material than the anterior half 44. Alternatively, a posterior-lateral half 46 can be made of a stiffer material than the anterior-lateral half 48.

In another preferred embodiment, while the center portion of the nucleus remains soft and maintains a low modulus, the periphery of the nucleus is made in such a way that it mimics the function of the annulus, e.g., it has a high tensile modulus and a relatively low compressive modulus. As the center portion of the nucleus is compressed and starts to bulge, the high tensile modulus periphery skin of the implant acts like a boundary layer to restrict the soft center from lateral bulging. The high tensile modulus periphery surface of the implant can be achieved by heat treatment or chemical treatment (chemical crosslink) on said surface.

The surface of the implants can either be smooth or have transverse grooves (not shown) to increase the stability of the prosthesis in the disc cavity. In the natural human disc both the superior and inferior surfaces are convex. Similarly, it is preferable that the prosthetic nucleus have convex surfaces on both sides so that it will fit tightly and evenly in the cavity created by the discectomy procedure. A tight fit will allow the load to be evenly distributed on the prosthetic nucleus and avoid excessive loading on particular parts of the implant.

The present invention shows reduced lateral bulging when tested under unconstrained conditions. Such diminished bulging at certain sections in the disc results in less hoop stress on the area where the annulus is thin, weak or injured than on the area where the annulus is thick, strong or undamaged. This reduced hoop stress reduces the risk of further damage to the annulus.

EXAMPLE 1

Figure 15:
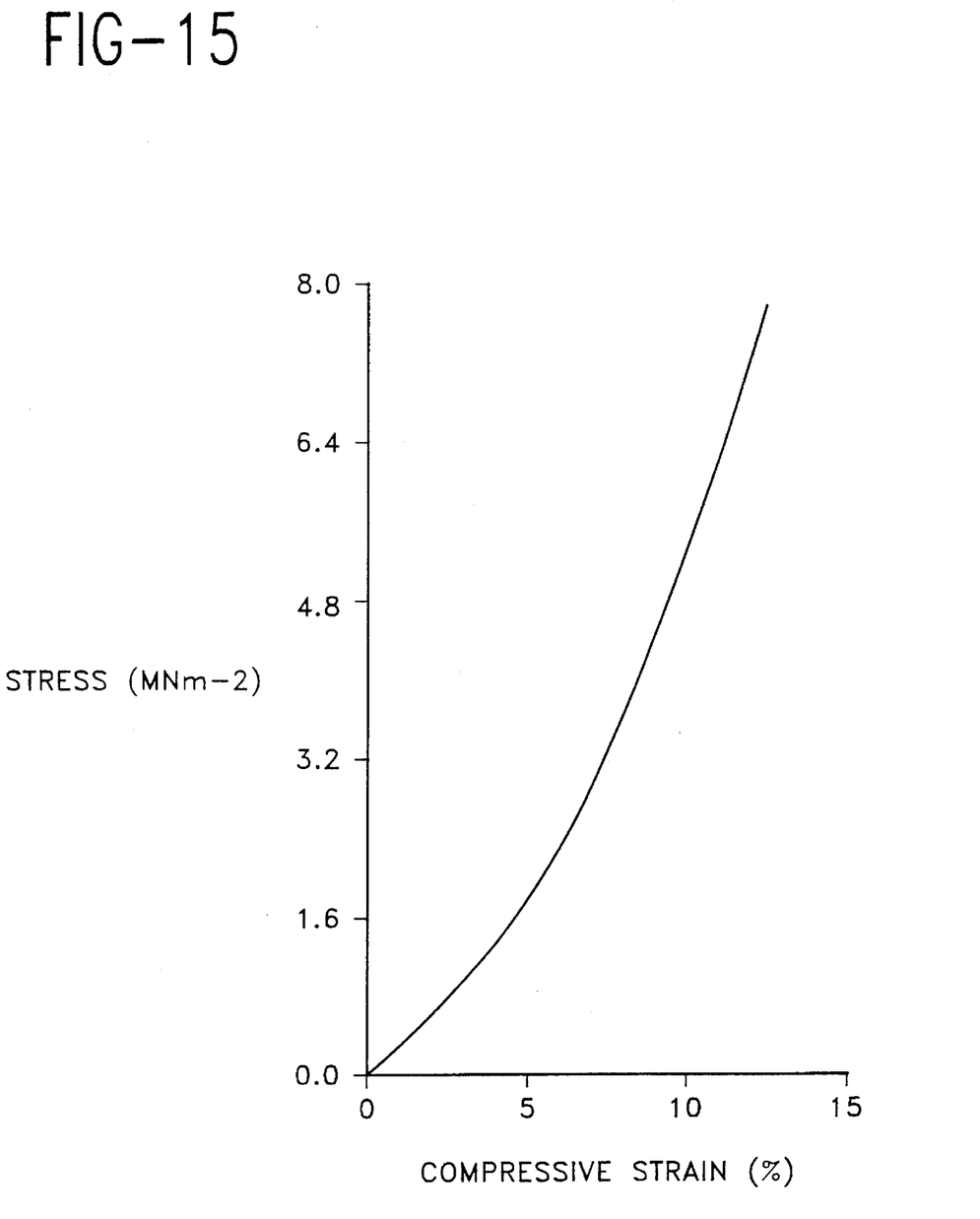
FIG. 15 is a graph showing the result of a stress vs. strain test of a PVA hydrogel.

The stress vs. strain curve of the PVA hydrogel of 74% water content made from 10–25% PVA powder as described above is presented in FIG. 15. To stimulate the constrained environment in which the nucleus is contained, a 1.0" in diameter and 0.8" in height PVA hydrogel disc was constrained in a connected three-piece test fixture having two rigid metal sleeves on each side with a flexible Tygon tube with wall thickness of ⅛" in the middle. All three pieces have an inner diameter of 1". The PVA hydrogel was then compressed between two 1" diameter solid cylinders inserted in either end of the test fixture and compressed in an INSTRON® testing machine and the stress vs. strain curve was recorded. This setup, under the test stress range, would allow the hydrogel to bulge about 1–2 mm laterally, which is close to the lateral bulging reported previously in human spinal disc tests (Reuber, M., et al, Journal of Biomechanical Engineering, volume 104, 1982, p. 187). Again, the extent of directional bulging of the prosthetic nucleus of the present invention would still be largely dependent on the restoring forces of the annulus. This stress vs. strain curve of the PVA hydrogel demonstrated that the PVA hydrogel offers similar or superior load resistant characteristics to the intervertebral disc. A compressive load of up to 4000 N was exerted on the hydrogel, indicating that the hydrogel is strong enough to withstand a load in excess of those normally generated by the body in various postures.

EXAMPLES 4–22

The PVA hydrogel solutions described in Table 1 below are generally suitable for use in the present invention. (As used in Table 1, PVA means polyvinyl alcohol; MW means molecular weight; modulus (E) is in units of MegaPasquals (MPa); and the shrink coefficient is determined by dividing the PVA dimensions after solvent exchange by the PVA dimensions before solvent exchange.) For instance, a nucleus can comprise a stiff hydrogel (such as Examples 5 and 6) on the posterior side and a soft hydrogel (such as Examples 16–19) on the anterior side. Alternatively, the nucleus can comprise a uniform hydrogel and have one wall thicker than the other.

TABLE 1

| Example # | PVA CONC. | PVA HYDROLYZATION | MW | MIXED SOLVENT (RATIO) | WATER CONTENT | MODULUS E M Pa | SHRINK COEFFICIENT $\alpha$ |
|---|---|---|---|---|---|---|---|
| 4 | 20% | 99.7% | 78K | DMSO/$H_2O$ 85/15 | 69% | 1.33 | .907 |
| 5 | 15% | 99.7% | 78K | DMSO/$H_2O$ 85/15 | 73% | 0.90 | .782 |
| 6 | 15% | 99.7% | 78K | DMSO/$H_2O$ 50/50 | 78% | 0.50 | .856 |
| 7 | 15% | 98% | 78K | DMSO/$H_2O$ 85/15 | 81% | 0.28 | .865 |
| 8 | 12.5% | 99.7% | 108K | DMSO/$H_2O$ 85/15 | 75% | 0.62 | .852 |
| 9 | 12.5% | 98% | 78K | DMSO/$H_2O$ 85/15 | 82% | 0.27 | .899 |
| 10 | 10% | 99.7% | 108K | DMSO/$H_2O$ 85/15 | 74.5% | 0.66 | .787 |
| 11 | 10% | 99.7% | 78K | DMSO/$H_2O$ 85/15 | 76.0% | 0.47 | .764 |
| 12 | 10% | 99% | 133K | DMSO/$H_2O$ 50/50 | 82.3% | 0.25 | .855 |
| 13 | 10% | 99.7% | 108K | DMSO/$H_2O$ 50/50 | 80% | 0.34 | .901 |
| 14 | 10% | 99.7% | 78K | DMSO/$H_2O$ 50/50 | 82% | 0.28 | .837 |
| 15 | 10% | 99.7% | 78K | DMSO/$H_2O$ 35/65 | 88% | 0.13 | .844 |
| 16 | 10% | 99.7% | 78K | DMSO/$H_2O$ 25/75 | 90% | 0.07 | 1.006 |
| 17 | 10% | 98% | 78K | DMSO/$H_2O$ 85/15 | 84% | 0.17 | .844 |
| 18 | 10% | 98% | 78K | DMSO/$H_2O$ 72/28 | 84.4% | 0.14 | .854 |
| 19 | 10% | 98% | 78K | DMSO/$H_2O$ 60/40 | 85% | 0.11 | .852 |
| 20 | 10% | 98% | 78K | DMSO/$H_2O$ 50/50 | 86.6% | 0.105 | .835 |
| 21 | 7.5% | 99.7% | 78K | DMSO/$H_2O$ 85/15 | 78% | 0.30 | .737 |
| 22 | 7% | 99.7% | 78K | DMSO/$H_2O$ 50/50 | 84% | 0.15 | .714 |

EXAMPLE 2

Figure 11A:
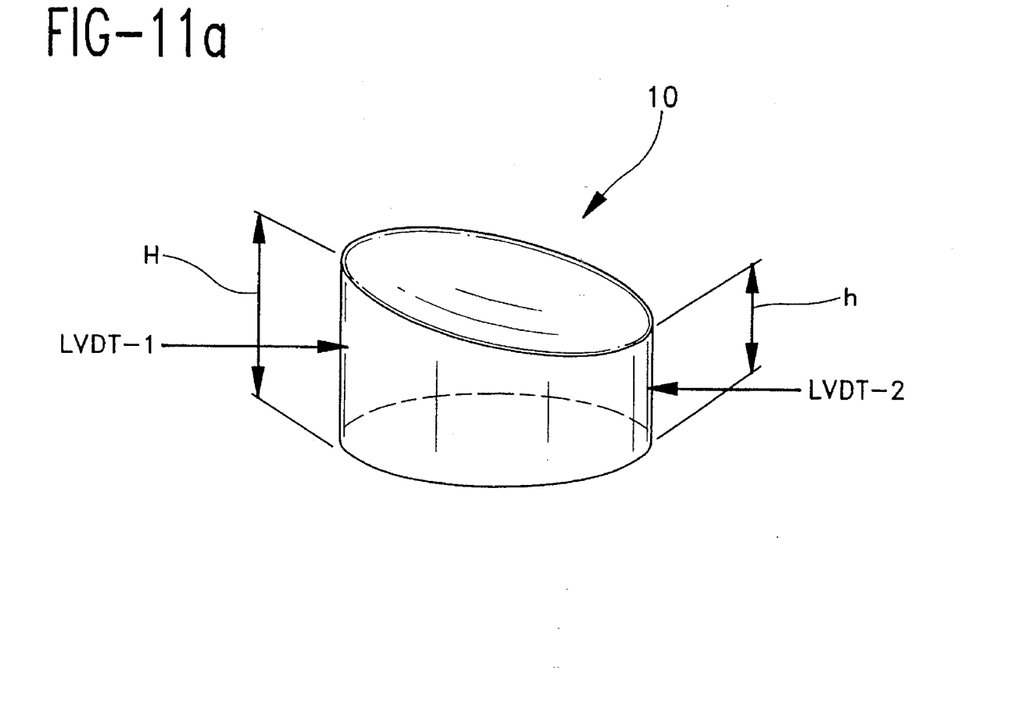
Figure 11B:
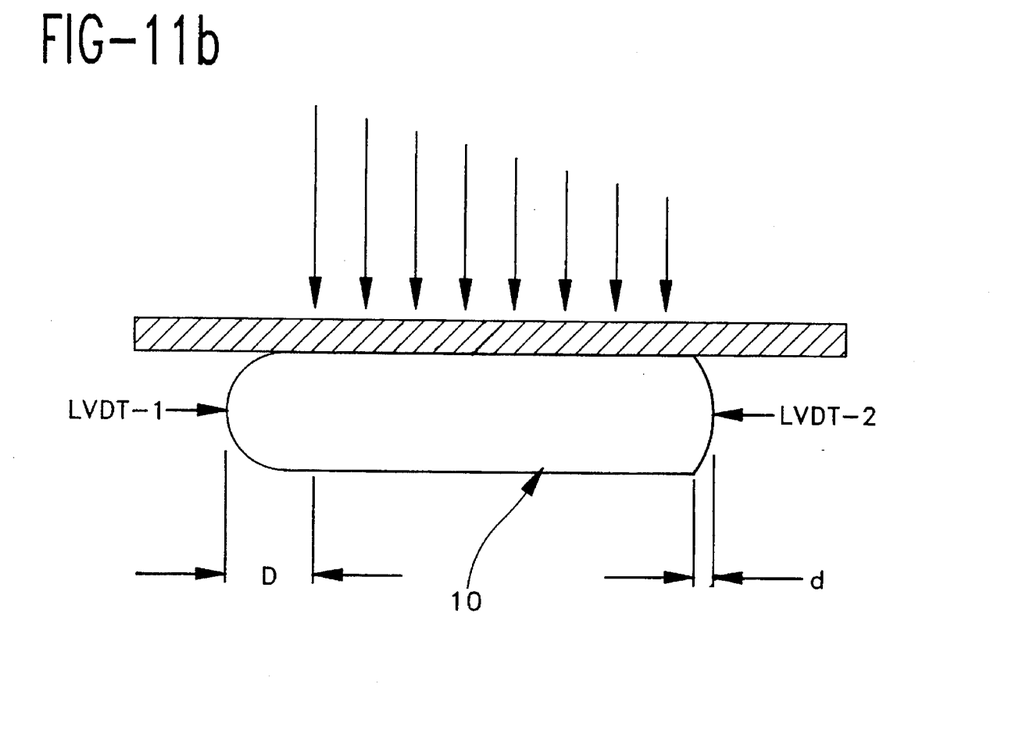

With reference to FIG. 11, a round hydrogel disc with diameter 1.212" and height (H) of thicker side 0.765" and height (h) of thinner side 0.603", as shown in FIG. 11 (a), was compressed with a compressive load of 12 N. Two Linear Variable Differential Transformers (LVDT) were placed in contact with the thick and thin side walls before the loading. The disc was loaded, and the lateral bulge of the two sides was recorded (FIG. 11 (b)). At 12 N, it was found that the bulge (D) on the thick side was 4.31 mm and the bulge (d) on the thin side was 1.49 mm.

EXAMPLE 3

Figure 12A:
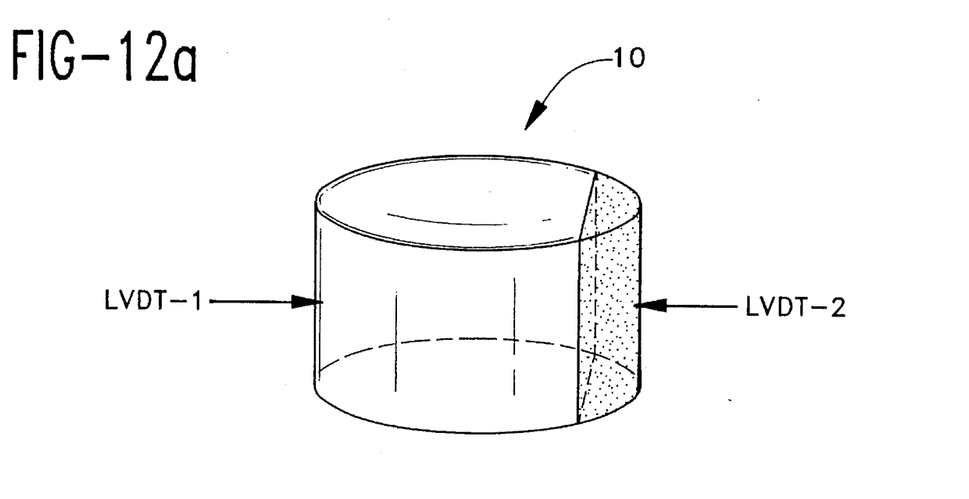
Figure 12B:
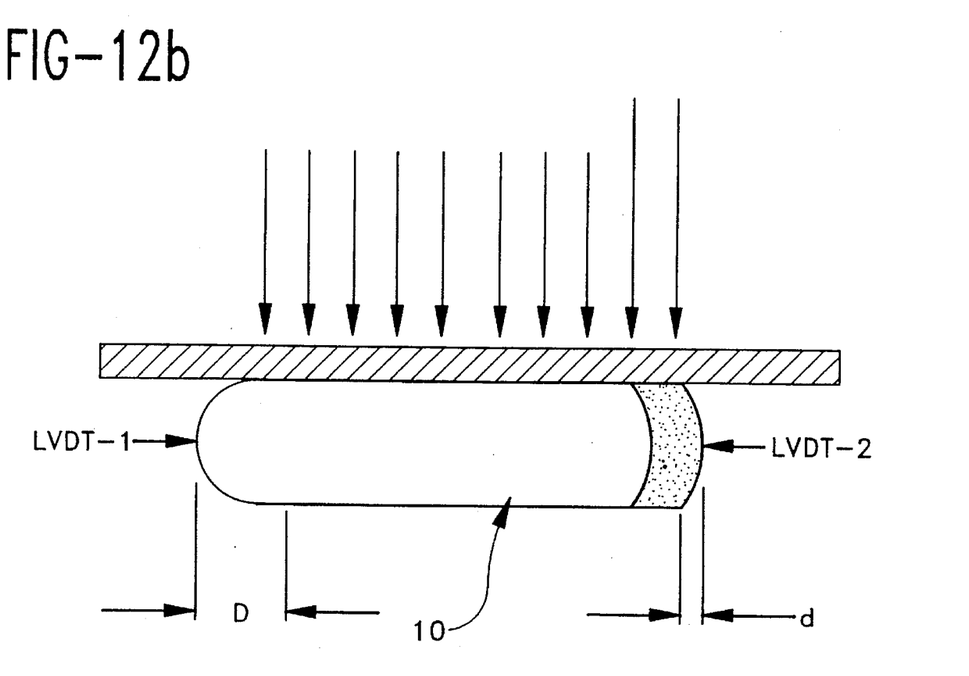

With reference to FIG. 12, a round hydrogel disc with diameter of 1.308" and height 0.912", as shown in FIG. 12 (a), was molded in such a way that about ⅕ of the width has the formulation of Example 4 in Table 1 and ⅘ of the width has the formulation of Example 18 in Table 1. The dense dot matrix represents the formulation of Example 4, and the non-shaded area represents the formulation of Example 18. The disc was loaded to 10 N and two LVDT's were placed on both soft and stiff sides of the disc. It was found that the bulge (D) on the soft side was 1.55 mm and the bulge (d) on the stiff side was 0.97 mm (FIG. 12 (b)).

Figure 13A:
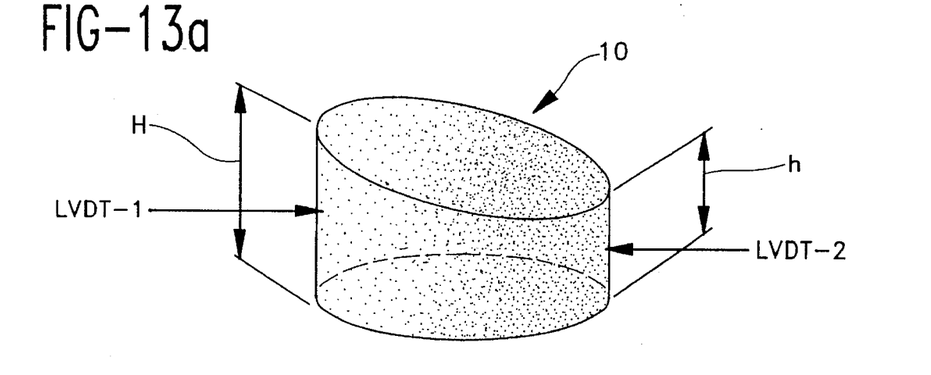
Figure 13B:
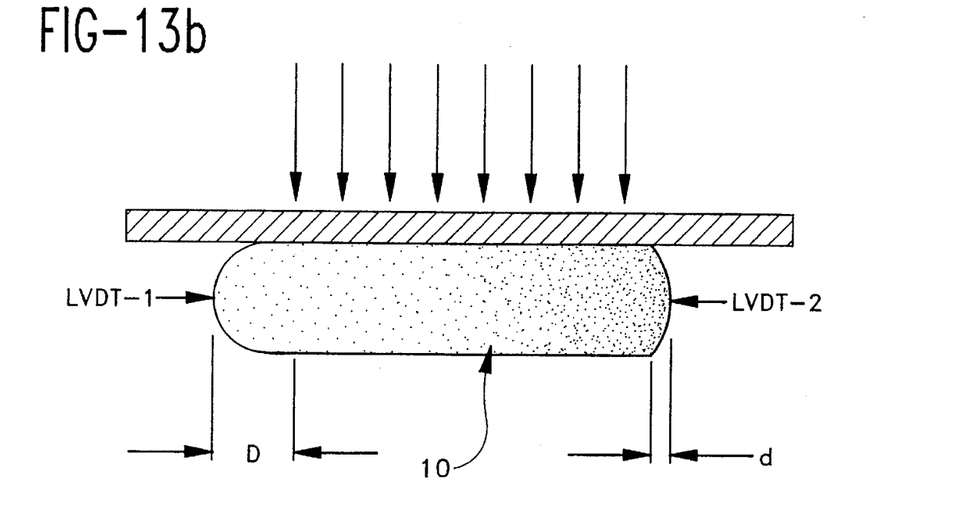

An especially preferred embodiment shown in FIG. 7 is a nucleus having at least part of the periphery both stiffer and thinner than other parts of the periphery. As indicated by the arrows in FIG. 11 (b), the stress on the thick side of the disc will be greater than the stress on the thin side of the disc. If the thickness variation on the different sides is too large, the stress on the thick side may increase to an undesirable extent and could exceed the normal stress on the disc. Thus, it is preferable to vary both thickness and stiffness in a single disc. It is most preferable to vary both stiffness and thickness gradually. FIG. 13 illustrates such a disc and shows how the bulge and stress distribution can be controlled. The denser dot matrix represents a stiffer material.

Figure 16:
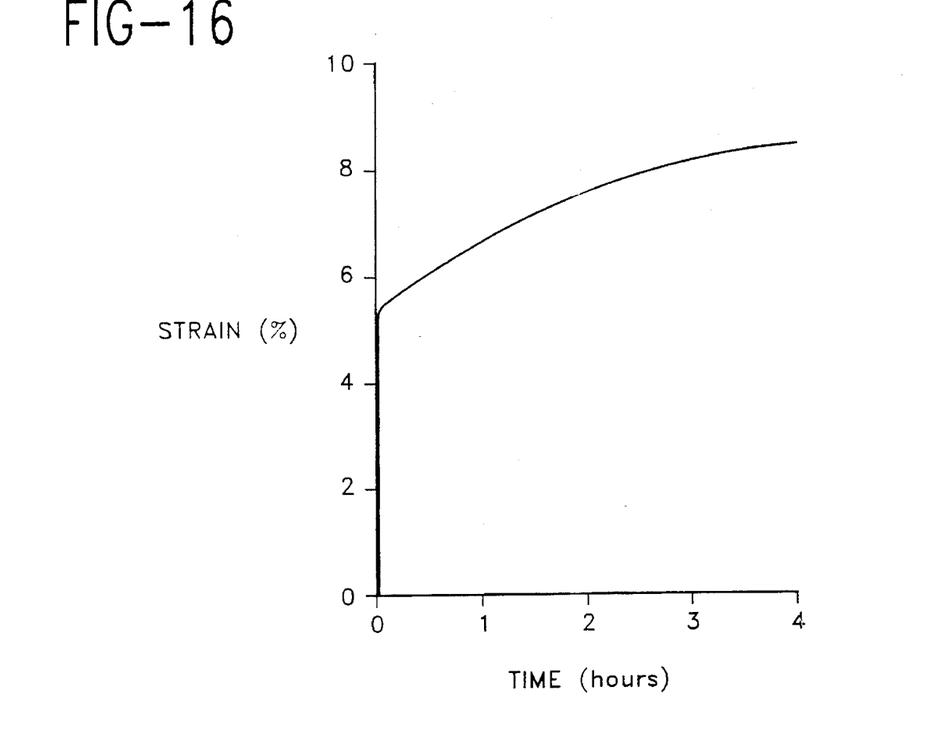
FIG. 16 is a graph showing the result of a creep test of a PVA hydrogel.

Because the natural nucleus is also primarily a hydrogel, the implanted hydrogel artificial nucleus can easily restore all the biomechanical functions of the nucleus which has been removed. Unlike the prior art prosthetic discs, the hydrogel nucleus in the present invention will restore the visco-elastic behavior of the disc due to the water binding capability of the prosthetic hydrogel. FIG. 16 presents the creep behavior of the same PVA hydrogel of 74% water content. This hydrogel was tested in the same device as described above in Example 1. The creep curve of the hydrogel is very similar to creep curve obtained in the human spinal disc reported elsewhere (Adam, M. A., and Hutton, W. C., *The Biology of the Intervertebral Disc,* Vol. II, 1988, p. 64). The initial, almost instantaneous, deformation in the disc arises mainly from a rearrangement of the collagen network in the annulus.

Figure 17:
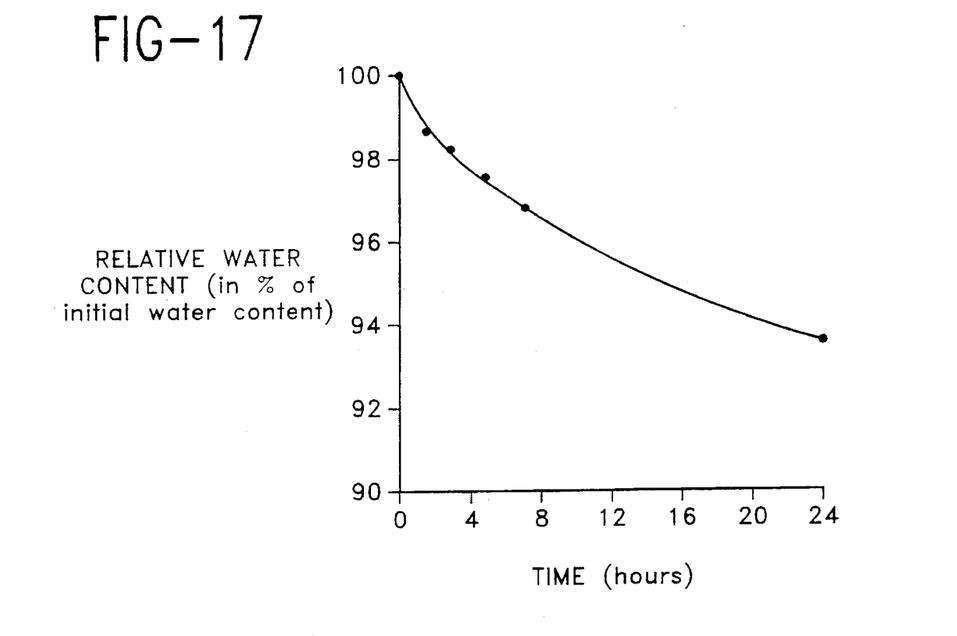
FIG. 17 is a graph showing the result of water content change vs. time of a PVA hydrogel under constant compressive load.

The initial deformation in this case is mainly due to the stretching of the Tygon tube. If the load is maintained, the disc continues to deform or creep largely because the fluid in the nucleus is being squeezed out. This is shown in FIG. 17 in which the percentage of water relative to the initial water content was plotted vs. time when constant load was applied. This visco-elastic characteristic, as mentioned above, is critical in withstanding the mechanical load and keeping the fluid flowing in and out of the disc.

The implantation of prosthetic nucleus 10 can be performed in conjunction with a discectomy operation, such as discectomy or microdiscectomy, percutaneous discectomy, or chemonuclealysis. Because the properties of the hydrogel prosthetic nucleus of the present invention are similar to those of the nucleus material, the herniated nucleus can be partially or totally replaced by the hydrogel prosthetic nucleus. Due to its small size, a posterior lateral approach can be used to implant the dehydrated hydrogel disc. This significantly reduces the difficulty and the risk of the operation.

The volume of a hydrogel nucleus of 80% water content will reduce by about 80% (to 20% of its original volume) when dehydrated. Consequently, the surgeon does not need to jack apart the vertebrae adjacent to a damaged disc as required by, for example, the device disclosed in U.S. Pat. No. 4,772,287. The height of the dehydrated prosthetic nucleus, when inserted, is smaller than the disc space. Furthermore, the rigidity of the dehydrated prosthetic nucleus will help the surgeons to manipulate the prosthetic nucleus during the operation. After implantation, the hydrogel nucleus of the present invention swells slowly in the body to a predetermined height which is enough to maintain the space between the vertebral body. The swelling process normally takes several hours to two days depending on the size of the prosthetic nucleus and type of hydrogel.

While several examples of the present invention have been described, it is obvious that many changes and modifications may be made thereunto without departing from the spirit and scope of the invention.

We claim:

1. A prosthetic nucleus for implanting into a disc space after removal of a degenerated or damaged nucleus of an intervertebral disc, said prosthetic nucleus comprising:

a biologically compatible hydrogel material having, when fully hydrated, a size and shape generally conforming to a natural nucleus or to the shape of a cavity created after removal of the degenerated or damaged nucleus; a water content of from about 30% to about 90%; and a compressive strength of about 4 $MNm^{-2}$ or greater; and said prosthetic nucleus having a prosthetic nucleus periphery wherein at least part of the prosthetic nucleus periphery exhibits diminished lateral bulging in comparison to other parts of the prosthetic nucleus periphery, wherein said nucleus has a modulus within the range from about 0.1 to about 1.5 MPa, wherein said nucleus has a softest part, and wherein the modulus of the nucleus varies such that at least part of the prosthetic nucleus periphery has a modulus of at least about 10% more than the softest part of the nucleus, wherein the nucleus has an anterior periphery and a posterior periphery, and at least part of the posterior periphery has a modulus of at least about 10% more than the modulus of at least part of the anterior periphery.

2. The prosthetic nucleus as set forth in claim 1 wherein said modulus of the prosthetic nucleus periphery gradually increases from the anterior side to the posterior side.

3. A prosthetic nucleus for implanting into a disc space after removal of a degenerated or damaged nucleus of an intervertebral disc, said prosthetic nucleus comprising:

a biologically compatible hydrogel material having, when fully hydrated, a size and shape generally conforming to a natural nucleus or to the shape of a cavity created after removal Of the degenerated or damaged nucleus; a water content of from 30% to 90%; and a compressive strength of 4 $MNm^{-2}$ or greater; and said prosthetic nucleus having a prosthetic nucleus periphery wherein said nucleus has a modulus within the range from 0.1 to 1.5 MPa, wherein the nucleus has a softest part, and wherein the modulus of the nucleus varies such that at least part of the prosthetic nucleus periphery has a modulus of at least 10% more than the softest part of the nucleus; and wherein the nucleus periphery has a nucleus periphery wall which varies in height by at least 1 mm., wherein the nucleus has an anterior periphery and a posterior periphery, and at least part of the posterior periphery has both (a) a modulus of at least 10% more than the modulus of at least part of the anterior periphery, and (b) a wall thickness of at least 1 mm more than the wall thickness of at least part of the anterior wall.

4. The prosthetic nucleus as set forth in claim 3 wherein the modulus of the nucleus periphery gradually increases from the anterior side to the posterior side, and the height of the nucleus gradually increases from the posterior side to the anterior side.

* * * * *